Jan. 15, 1974 M. M. DROPINSKI Plant Pat. 3,437
CARNATION PLANT
Filed March 22, 1972
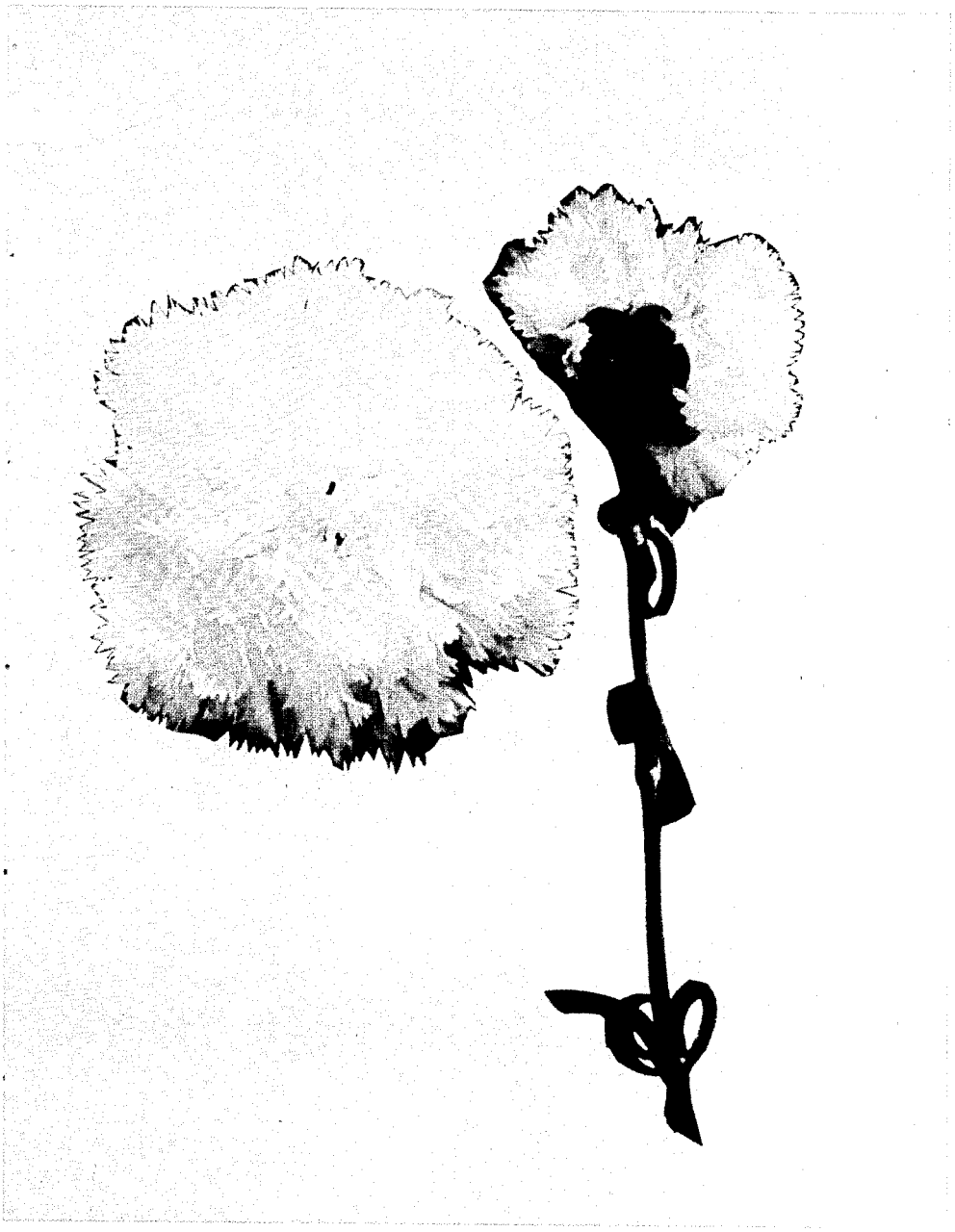

United States Patent Office

Plant Pat. 3,437
Patented Jan. 15, 1974

3,437
CARNATION PLANT

Marion M. Dropinski, Colorado Springs, Colo., assignor to Broadmoor Hotel, Inc., Colorado Springs, Colo.

Filed Mar. 22, 1972, Ser. No. 237,210
Int. Cl. A01h *5/00*
U.S. Cl. Plt.—70 1 Claim The present invention relates to a new and distinct variety of carnation plant which originated as a seedling of the Sidney Littlefield variety.

The primary objective of the breeding was to produce a new carnation variety of a pure white with no variegation, which has longer stems, stronger and larger flowers and which are longer lasting than the Littlefield variety. Accompanying color photographs show in approximately true color a full front view of a typical specimen of the flower of this new variety, and a near view of the flower indicating the structure of the calyx portions of the stems and foliage. The following novel and distinctive features are outstanding and particularly differentiate a new variety from its seed parent as well as from all other varieties:

THE PLANT

Growth habit: The growth of the stems is vigorous and upright, usually to a height of 30 to 34 inches. The shoots are strong and the stems are up to ¼-inch in diameter with no grassy growth. The cuttings root easily.

Disease resistance: The plant is very resistant to usual diseases affecting carnations.

Flowering habits: The plant is a continuous bloomer that is unusually prolific in flower production. The plant usually has disbuds which must be removed. The flowers are very full with lacy petals. The plant usually produces ten buds, of which nine are disbuds and removed leaving a terminal bud on the stem.

Foliage: The foliage quantity is average with the leaves usually one to two inches apart. The lower leaves are usually six inches long and about ½-inch in width. The lower leaves are dark green covered with gray bloom. The substance of the leaves is heavy and waxlike. Very healthy leaves have a double curl. The stems are usually the same color as the leaves, are unusually heavy and quite strong and stiff, usually 30–34 inches.

THE FLOWER

Blooming habit: Recurrent—continuous

Bud:

*Shape.*—Bulged but tapered.

*Size.*—Large. When color begins to show about 1¼-inches.

*Opening.*—Typical opening speed.

Flower:

*Size.*—Large, 4 to 4½-inches.

*Form.*—The flower is full with an exceptional amount of large, lacy petals. The flower is unusually heavy, about 3 ounces. The outer petals average 1¾-inches across, are irregularly fringed, scalloped and fairly deep cut.

*Color.*—Individual petals are a pure white with no variegation and fairly uniform.

*Petalage.*—Average petalage is about 75 per blossom.

*Calyx.*—Very large and strong, and it does not split easily.

*Petals.*—Irregularly fringed, scalloped and fairly deep cut. Outer petals large.

*Fragrance.*—Moderate.

*Longevity.*—Cut flowers are unusually long lasting. In a 72° F. home environment, cutting a small portion from the bottom of the stem daily and changing water daily, the flowers last 16 days or longer.

Reproductive organs:

*Ovary.*—Positioned in the center of the flower, being unusually large—about ⅜-inch compared to the normal ¼-inch for other carnations.

*Pistils.*—About ⅜-inch with a white bottom and a green center. The pistils do not have curled tips and are not visible in the opening flower.

*Stamen.*—The relative number of stamens in the blossom is nine, they are straggling and white in color.

I claim:

1. A new and distinctive variety of carnation plant of the Littlefield variety, substantially as herein shown and described, characterized particularly as to novelty by its large blossoms of pure white with no variegation, longer and stronger stems, with the flowers lasting longer.

No references cited.

ROBERT E. BAGWILL, Primary Examiner